Figure 1:
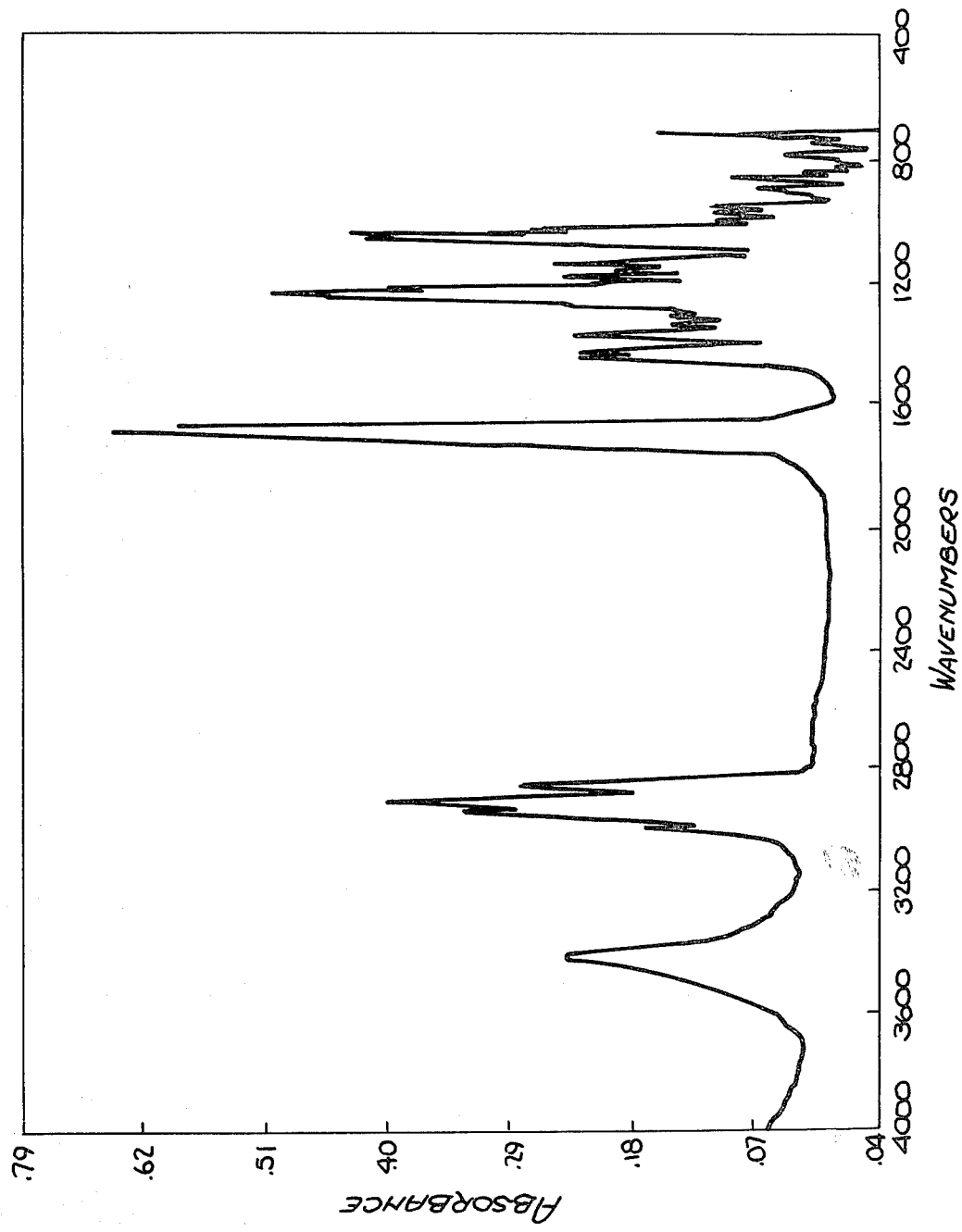
Figure 2:
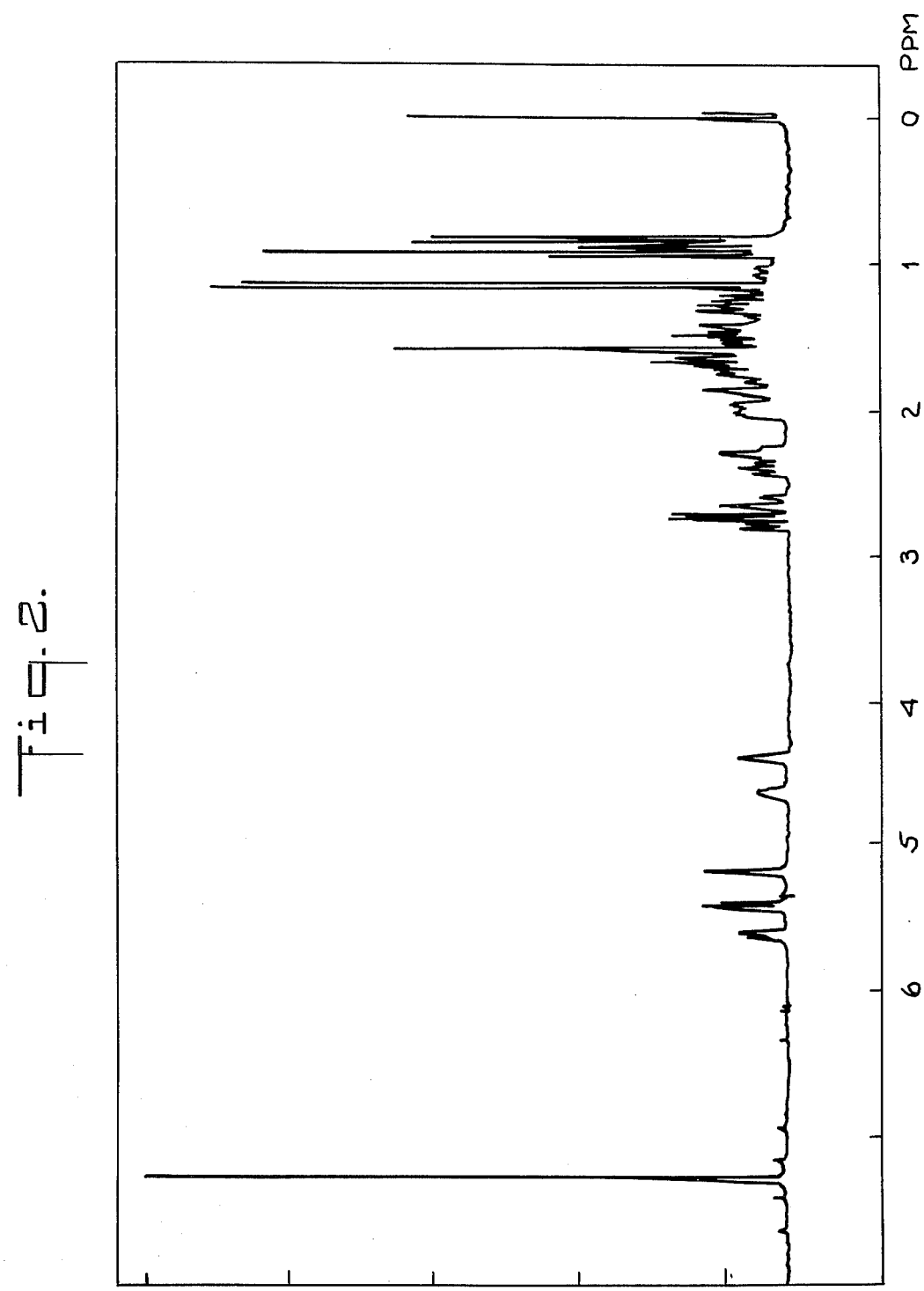

United States Patent [19]

Gullo et al.

[11] 4,432,996
[45] Feb. 21, 1984

[54] HYPOCHOLESTEROLEMIC FERMENTATION PRODUCTS AND PROCESS OF PREPARATION

[75] Inventors: Vincent P. Gullo; Tony Y. K. Lam, both of Edison; Richard L. Monaghan, Somerset, all of N.J.

[73] Assignee: Merck & Co., Inc., Rahway, N.J.

[21] Appl. No.: 378,934

[22] Filed: May 17, 1982

Related U.S. Application Data

[62] Division of Ser. No. 207,508, Nov. 17, 1980, Pat. No. 4,343,814.

[51] Int. Cl.³ .................. C07C 69/28; C07C 69/76; A61K 31/22
[52] U.S. Cl. ................... 424/311; 560/119; 560/256
[58] Field of Search ............... 560/119, 256; 424/311

[56] References Cited

U.S. PATENT DOCUMENTS

| | | | |
|---|---|---|---|
| 3,983,140 | 9/1976 | Endo et al. | 549/292 |
| 4,049,495 | 9/1977 | Endo et al. | 435/125 |
| 4,137,322 | 1/1979 | Endo et al. | 560/119 |
| 4,231,938 | 11/1980 | Monaghan et al. | 560/256 |
| 4,293,496 | 10/1981 | Willard | 562/501 |
| 4,319,039 | 3/1982 | Albers-Schonberg | 560/119 |
| 4,346,227 | 8/1982 | Terahara et al. | 560/119 |

FOREIGN PATENT DOCUMENTS 33538 8/1981 European Pat. Off. ............ 424/311

*Primary Examiner*—Natalie Trousof
*Assistant Examiner*—Patricia M. Scott

*Attorney, Agent, or Firm*—William H. Nicholson; Mario A. Monaco

[57] ABSTRACT

Substances isolated after cultivation of a micoorganism belonging to the genus Penicillium in a culture medium comprises compounds which have strucures:

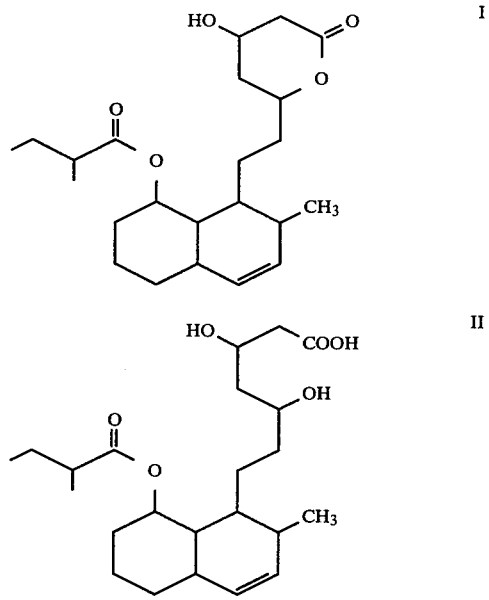

Together with salts and esters of the carboxylic acid, these compounds form a class of highly active hypocholesterolemic and hypolipemic medicaments.

12 Claims, 2 Drawing Figures

HYPOCHOLESTEROLEMIC FERMENTATION PRODUCTS AND PROCESS OF PREPARATION

This is a division of application Ser. No. 207,508, filed Nov. 17, 1980, now U.S. Pat. No. 4,343,814.

SUMMARY OF THE INVENTION

This invention relates to hypocholesterolemic products from the cultivation of a microfungus of the genus, Penicillium. More specifically, it relates to compounds of formulae I and II:

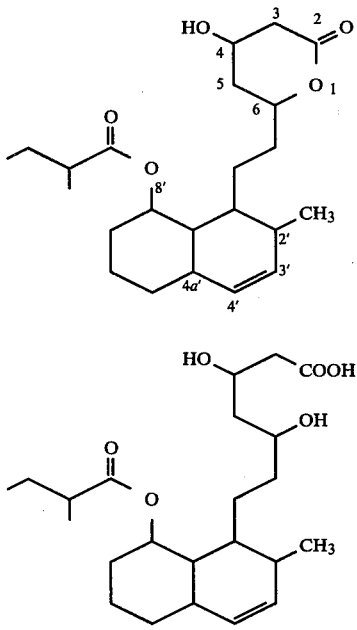

as well as pharmaceutically acceptable salts and lower alkyl and substituted alkyl esters of the carboxylic acids in which the possible substituent is phenyl, dimethylamino or acetylamino. The invention also relates to a process of cultivating the microfungus and isolating from the medium a hypocholesterolemic compound of the above structures. These new compounds have excellent properties of inhibiting cholesterol biosynthesis and are useful against hypercholesterolemia and hyperlipemia.

BACKGROUND OF THE INVENTION

Because of the possible connection between high blood cholesterol and atherosclerosis, many efforts have been made to find ways and substances which would reduce the cholesterol in the mammalian body. One of these ways is to inhibit in mammals the body's ability to synthesize cholesterol.

Recently, Endo et al., described (U.S. Pat. Nos. 4,049,495 and 3,983,140) a fermentation product obtained by cultivation of a microorganism of the genus Penicillium and isolation from the medium. They called it ML 236 B and determined its structure together with two related compounds 236 A and 236 C. Its structure, under the name compactin, was also determined by A. G. Brown, T. C. Smale, T. J. King, *J. Chem. Soc.* (Perkin I) 1165 (1975). This compound has been found to be an inhibitor, in vivo, of the biosynthesis of cholesterol.

DESCRIPTION OF THE INVENTION

It has been found that the cultivation of the same microorganism employed by Endo, produces compounds I and II that are also very potent inhibitors of the biosynthesis of cholesterol in mammals.

The pharmaceutically acceptable salts of compound II, that are also part of this invention, include those formed from cations such as sodium, potassium, aluminum, calcium, lithium, magnesium, zinc, ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, tris(hydroxymethyl)aminomethane, and tetramethylammonium.

The compounds of this invention are highly useful as antihypercholesterolemic agents for the treatment of atherosclerosis, hyperlipemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg. to 2000 mg. (preferably 2 to 100 mg) which may be given in two to four divided doses. Higher doses may be favorably employed as required.

The compounds of this invention also have useful antifungal activities. For example, they may be used to control strains of Penicillium sp., *Aspegillus niger,* Cladosporium sp., *Cochliobolus miyabeanus* and *Helminthosporium cynodnotis.* For those utilities they are admixed with suitable formulating agents, powders, emulsifying agents or solvents such as aqueous ethanol and sprayed or dusted on the items to be protected.

In another aspect of this invention, it relates to a process for producing the compounds of this invention which comprises cultivating a microorganism belonging to the genus Penicillium and then recovering said compounds of this invention from the cultured broth.

The microorganisms which may be employed in this invention are the ones belonging to the genus Penicillium and, there is, for instance, mentioned *Penicillium citrinum* which has been deposited under an accession No. 2609 with Technical Research Institute of Microbial Industry, Agency of Industrial Science & Technology, Ministry of International Trade and Industry, Japan, and also NRRL-8082 in the Northern Regional Research Laboratory, Northern Central Region, Agricultural Research Service, U.S. Department of Agriculture, at Peoria, Ill., U.S.A.

Of particular importance in the production of Compounds I and II is a natural isolate of the above-identified species (NRRL-8082) which has been deposited in the American Type Culture Collection with Accession Number, ATCC 20606.

Although this invention is explained hereinbelow principally with respect to the specific strain, it is well-known in the art that various properties of all microorganisms belonging to the genus Penicillium are not definite, but the microorganisms of the genus Penicillium may be easily varied naturally and artificially. It is, accordingly, to be noted that all strains which are of the genus Penicillium and capable of producing compounds I and II, including varieties and mutants, are contemplated and usable in this invention.

The above strain is known and its morphological properties are reported in K. B. Raper and C. Thom; A Manual of the Penicillia, the Williams and Wilkins Company, 1949.

The culture of these organisms to produce the novel compounds is carried out in aqueous media such as those employed for the production of other fermentation products. Such media contain sources of carbon, nitrogen and inorganic salts assimilable by the microorganism.

In general, carboydrates such as sugars, for example, glucose, fructose, maltose, sucrose, xylose, mannitol and the like and starches such as grains, for example, oats, ryes, malt extract, cornstarch, corn meal, or oils such as glycerol, corn oil, soybean oil and the like can be used either alone or in combination as sources of assimilable carbon in the nutrient medium. The exact quantity of the carbon source or sources utilized in the medium depends in part upon the other ingredients of the medium but, in general, the amount of carbon sources usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include for example, yeast hydrolysates, primary yeast, soybean meal, cottonseed flour, hydrolysates of casein, corn steep liquor, distiller's solubles or tomato paste and the like. The sources of nitrogen either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, magnesium, calcium, phosphate, sulfate, chloride, carbonate, and like ions. Also included are trace metals such as cobalt, copper, boron, manganese, iron, zinc and molybdenum.

It should be noted that the media described in the Examples are merely illustrative of the wide variety of media which may be employed, and are not intended to be limitative. Specifically, the carbon sources used in the culture media to produce the novel compounds of this invention included dextrose, glycerol, malt extract and oatmeal. Included as nitrogen sources were autolyzed yeast, tomato paste, oatmeal, malt extract and corn steep liquor. The major added ionic component was $CaCl_2$ and traces of Fe, Mn, Mo, B and Cu were also present.

The fermentation is carried out at temperatures ranging from about 22° to 26° C.; however, for optimum results it is preferable to conduct the fermentation at temperatures of from about 24° to 25° C. The pH of the nutrient media suitable for growing the Penicillium culture and producing the novel compounds can vary from about 4.0 to 7.0.

Although the novel compounds are produced by both surface and submerged culture, it is preferred to carry out the fermentation in the submerged state. A small scale fermentation is conveniently carried out by inoculating a suitable nutrient medium with the Penicillium culture and, after transfer to a production medium, permitting the fermentation to proceed at a constant temperature of about 25° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for 1–3 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 25° C. This method of producing the novel compounds is particularly suited for the preparation of large quantities.

The compounds are conveniently isolated from the fermentation broth as the lactone (I) by acidification to about pH 3–5, extraction with an inert organic solvent such as ethyl acetate, back extraction with dilute alkali, acidification, ethyl acetate extraction, concentration, lactonization and chromatography.

Compound I can be hydrolyzed with bases such as NaOH to yield the salts such as the sodium salt of Compound II. The use of bases with other pharmaceutically acceptable cations affords salts of these cations. Careful acidification of the salts affords the hydroxy acid II. The hydroxy acid II or its ammonium salt can be converted to Compound I by refluxing in toluene. Treating Compound I under acidic or basic catalysis with methanol, ethanol, propanol, or butanol or with phenyl, dimethylamino, or acetylaminoalkanols yields the corresponding esters of Compound II which also form a part of this invention.

EXAMPLE 1

Fermentative Production of Compounds I and II

A. Fermentation:

A natural isolate of *Penicillium citrinum*, NRRL 8082 was used to prepare a yeast-malt extract (YME) slant which was incubated for 2 weeks at 28° C.

A portion (1/5) of the slant (MF-4870a) was used to inoculate each of 5 unbaffled seed flasks (250 ml) containing 44 ml of KF seed medium with $CaCl_2$. They were incubated for 3 days at 28° C., and 220 rpm. A portion of the seed growth (about 1.5 ml) was used to inoculate each of 100 production medium flasks (250 ml unbaffled) containing 40 ml of LM Production Medium Without Malt Extract. The production flasks were incubated for 4 days at 25° C.

Another group of production medium flasks (140), each containing 40 ml of LM Production Medium Without Modification were inoculated and incubated under the same conditions as previously described. The broths from both fermentations were combined.

The various media employed in the foregoing fermentations are:

| YME Slant | |
|---|---|
| Dextrose | 4 g./l. |
| Malt Extract | 10 g./l. |
| Yeast Extract | 4 g./l. |
| Agar | 20 g./l. |
| Dist. Water | to 1 liter |
| pH | 7.0 |
| KF Seed Medium with $CaCl_2$ | |
| $CaCl_2$ | 10 g. |
| Corn steep liquor | 5 g. |
| Tomatoe Paste | 40 g. |
| Oatmeal | 10 g. |
| Cerelose | 10 g. |
| Trace Element Mix | 10 ml. |
| Distilled Water | 1000 ml. |
| pH | 6.8 |
| Trace Element Mix | |
| $FeSO_4.7H_2O$ | 1 g. |
| $MnSO_4.4H_2O$ | 1 g. |
| $CuCl_2.2H_2O$ | 25 mg. |
| $CaCl_2$ | 100 mg. |
| $H_3BO_3$ | 56 mg. |
| $(NH_4)_6Mo_7O_{24}.4H_2O$ | 19 mg. |
| $ZnSO_4.7H_2O$ | 200 mg. |
| Distilled Water | 1000 ml. |
| LM Production Medium Without Malt Extract | |
| Dextrose | 20 g. |
| Glycerol | 20 ml. |
| Ardamine pH | 10 g. |
| $CoCl_2.6H_2O$ | 8 mg. |
| Polyglycol p 2000 | 0.25% |
| Distilled Water | 1000 ml. |
| pH | 7.0 |
| LM Production Medium Without Modification | |
| Dextrose | 20 g. |
| Glycerol | 20 ml. |
| Ardamine pH | 10 g. |
| Malt Extract | 20 g. |
| $CoCl_2.6H_2O$ | 8 mg. |
| Polyglycol p 2000 | 0.25% |
| Distilled Water | 1000 ml. |
| pH | 7.0 |

B. Isolation

The combined whole broth (10.3 liters) was filtered and the mycelia cake was washed with 2.5 liters of deionized water. The combined filtrate and wash was adjusted to pH 4.0 with 1N hydrochloric acid. The aqueous solution was extracted with 7 liters of ethyl acetate and the extract was back-extracted with 3×2 liters of aqueous sodium hyroxide solution. The combined sodium hydroxide extract was adjusted to pH 3.8 with 1N hydrochoric acid and extracted with 2 liters and 1 liter of ethyl acetate. The combined ethyl acetate solution was dried over anhydrous $Na_2SO_4$, filtered and concentrated to dryness. The oily residue was dissolved in toluene and refluxed for 1 hour. The toluene solution was concentrated to dryness and the residue was dissolved in 18 ml of a mixture of n-hexane/toluene/methanol (4/1/1 by volume). This solution was loaded onto a 30 mm (ID)×40 cm. Sephadex LH-20 column equilibrated in the same solvent system. After eluting with 300 ml of solvent, a 10 ml fraction was obtained which was concentrated to an oil. High performance liquid chromatography (HPLC) on an ES Industries Chromega$^R$ column (9 mm×50 cm) using a mixture of acetonitrile/water (60/40 by volume) as the eluting solvent yielded 45 mg of dihydrocompactin (Compound I), m.w. 392.2560 by mass spectrum (calculated for $C_{23}H_{36}O_5$, 392.2558)

In KBr, the major IR peaks obtained from a Fourier Transform-IR (FTIR, Nicolet, Model 7199) (FIG. I) are at 1724, 1704, 1258, 1078 and 1070 $Cm^{-1}$. Of significance is a peak at 3005 $Cm^{-1}$ and the absence of a peak at 3030 $Cm^{-1}$.

A nuclear magnetic resonance spectrum (FIG. II) was obtained in $CDCl_3$ (~1 mg/0.5 ml) on a Varian SC-300 superconducting nmr spectrometer. The following are the peak positions given in ppm ($\delta$) relative to internal tetramethylsilane (TMS).

| $\delta$ | Assignment |
|---|---|
| 5.62 d,d,d (2.17, 4.5, 10.0) | $H_{3'}$(d?) |
| 5.43 d (10) | $H_{4'}$(c?) |
| 5.20 m | $H_{8'}$ |
| 4.63 m | $H_6$ |
| 4.39 m | $H_4$ |
| 2.75 d,d (17.5, 5.5) | $3-CH_2$ |
| 2.63 d,d,d (17.5, 4.0, 1.5) | |
| 2.39 m | $CH_3HCC\overset{O}{\underset{\diagdown}{\diagup}}$ |
| 2.29 m | $H_{4a'} + H_{5'}$ |
| 1.14 d | $CH_3CHC\overset{O}{\underset{\diagdown}{\diagup}}$ |
| 0.90 t | $CH_3CH_2$ |
| 0.84 d | $CH_3H_{5'}$ | d: doublet; m: multiplet; t: triplet

The evidence indicates the structure to be:

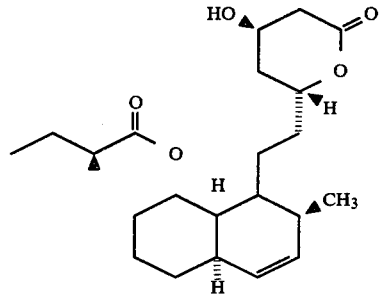

EXAMPLE 2

Alkali and Alkaline Earth Salts of Compound II

To a solution of 40 mg of the product of Example 1 in 2 ml of ethanol is added 1 ml of aqueous NaOH ($10^{-4}$ moles; 1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 3

Ammonium Salt of Compound II

The sodium salt from Example 2 is dissolved in 2 ml of water, cooled in ice and acidified slowly with 0.5M HCl. The mixture is extracted with ethyl acetate, back-extracted with water, dried over $MgSO_4$ and filtered. The filtrate is treated with anhydrous ammonia with stirring and cooling to precipitate the ammonium salt.

EXAMPLE 4

Ethylenediamine Salt of Compound II

To a solution of 0.50 g of the ammonium salt of Compound II in 10 ml of methanol is added 75 £ 1 of ethylenediamine. The methanol is stripped off under vacuum and the residue is triturated with acetone, stored in the cold, and filtered to obtain the ethylenediamine salt of Compound II.

EXAMPLE 5

Tris(hydroxymethyl)aminomethane Salt of Compound II

To a solution of 202 mg of the ammonium salt of Compound II in 5 ml of methanol is added a solution of 60.5 mg of tris(hydroxymethyl)aminomethane in 5 ml of methanol. The solvent is removed in vacuo and the residue triturated with a 1:1 mixture of acetonitrile:methanol. The desired tris(hydroxymethyl)aminomethane salt of Compound II is filtered off and dried.

EXAMPLE 6

L-Lysine Salt of Compound II

A solution of 0.001 mole of L-lysine and 0.0011 mole of the ammonium salt of Compound II in 15 ml of 85% ethanol is concentrated to dryness in vacuo. The residue is triturated with 10 ml of warm ethanol, cooled, and filtered to give the L-lysine salt of Compound II.

Similarly prepared are the L-arginine, L-ornithine, and N-methylglucamine salts of Compound II.

EXAMPLE 7

Tetramethylammonium Salt of Compound II

A mixture of 68 mg of Compound I in 2 ml of methylene chloride and 0.08 ml of 24% tetramethylammonium hydroxide in methanol is diluted with ether to cause precipitation of the tetramethylammonium salt of Compound II.

EXAMPLE 8

Preparation of Hydroxy Acid, Compound II

221 Mg of the ammonium salt of Compound II are dissolved in 4.5 ml of 65% ethanol, cooled in ice, acidified with abut 0.5 ml of 1M HCl to pH3, and evaporated at low temperature in a rotary evaporator to a volume of about 2 ml. 2 Ml more water are added, the mixture extracted into 2×3 ml of ethyl acetate, and backwashed with 1 ml of water, keeping all solutions cold in an ice bath. The extract is dried over MgSO4 and evaporated to dryness in vacuo to obtain the hydroxy acid as a colorless oil.

EXAMPLE 9

Ethyl Ester of Compound II

To a solution of 400 mg of the product, Compound I, in 100 ml of absolute ethanol is added 10 ml 0.1M sodium ethoxide in absolute ethanol. This solution is allowed to stand at room temperature for one hour, is then diluted with water and extracted twice with water, the ethyl acetate dried over anhydrous sodium sulfate is removed in vacuo to yield the ethyl ester of Compound II.

In like manner, by the use of equivalent amounts of methanol, propanol, butanol, isobutanol, t-butanol, amylalcohol, isoamylalcohol, 2-dimethylaminoethanol, benzylalcohol, phenethanol, 2-acetamidoethanol and the like, the corresponding esters are obtained.

What is claimed:

1. The compound:

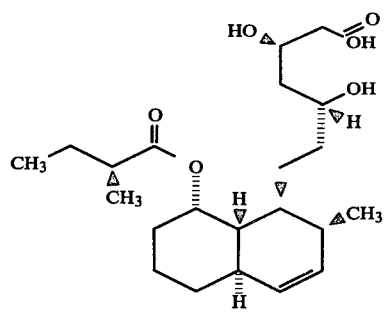

or a pharmaceutically acceptable salt or a lower alkyl ester or a substituted lower alkyl ester wherein the substituent is phenyl, dimethylamino, or acetylamino.

2. The pharmaceutically acceptable salts of the compound of claim 1, wherein the cation is derived from ammonia, ethylenediamine, N-methylglucamine, lysine, arginine or ornithine.

3. The ammonium salt of Compound II of claim 1.

4. The ethylenediamine salt of Compound II of claim 1.

5. The lower alkyl esters and substituted lower alkyl sters of the compound II of claim 1.

6. The ethyl ester of Compound II of claim 1.

7. An antihypercholesterolemic pharmaceutical composition comprising a pharmaceutical carrier and an effective antihypercholesterolemic amount of the compound:

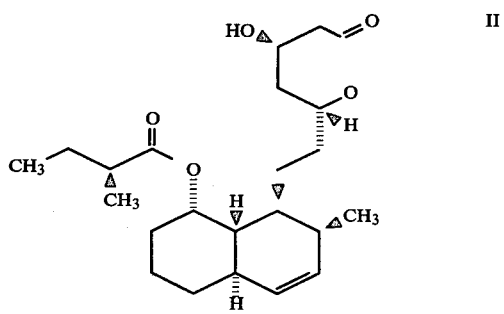

or a pharmaceutically acceptable salt or a lower alkyl ester or a substituted lower alkyl ester wherein the substituent is phenyl, dimethylamino, or acetylamino.

8. The composition of claim 7 wherein the compound is a pharmaceutically acceptable salt wherein the cation is derived from ammonia, ethylenediamine, N-methylglucamine, lysine, arginine or ornithine.

9. The composition of claim 7 wherein the compound is the ammonium salt of Compound II.

10. The composition of claim 7 wherein the compound is the ethylenediamine salt of Compound II.

11. The composition of claim 7 wherein the compound is a lower alkyl ester or substituted lower aklyl ester of Compound II.

12. The composition of claim 7 wherein the compound is the ethyl ester of Compound II.

* * * * *